United States Patent
Amici et al.

(12)

(10) Patent No.: US 6,180,681 B1
(45) Date of Patent: Jan. 30, 2001

(54) 2-CYCLOPENTEN-1-ONE AS AN INDUCER OF HSP70

(75) Inventors: Carla Amici, Rome; Giuliano Elia, Palestrina; Enrico Garaci, Rome; Antonio Rossi, Colledimacine; Maria Gabriella Santoro, Avellino, all of (IT)

(73) Assignee: Consiglio Nazionale Delle Ricerche, Rome (IT)

( * ) Notice: Under 35 U.S.C. 154(b), the term of this patent shall be extended for 0 days.

(21) Appl. No.: 09/202,553

(22) PCT Filed: Jun. 18, 1997

(86) PCT No.: PCT/EP97/03185

§ 371 Date: Dec. 16, 1998

§ 102(e) Date: Dec. 16, 1998

(87) PCT Pub. No.: WO97/48389

PCT Pub. Date: Dec. 24, 1997

(30) Foreign Application Priority Data

Jun. 18, 1996 (IT) .............................. RM96A0430

(51) Int. Cl.[7] ......................... A61K 31/12; A61K 31/015
(52) U.S. Cl. ......................... 514/690; 514/675; 514/763
(58) Field of Search .................................. 514/763, 690, 514/675

(56) References Cited

PUBLICATIONS

Amici et al, J of Virology, vol. 68 (11) pp 6890–99, 1994.*
Fukushima et al 98 CA 47110, 1982.*
Rossi et al 126 CA: 112777, 1996.*
Hungale et al 117CA: 27063, 1991.*
Lee et al 89 CA 99740, 1978.*
Halazy et al 118 CA 169497, 1992.*
Biological & Pharmaceutical Bulletin, 1995, 18 (12): 1784–1786, "Gastric Cytoprotective Activity of 2–Cyclopenten–1–one and Related Compounds", Alejandra O. Marla et al.*
Antiviral Research, 1995, 26(1): 83–96; "Antiviral Effect of Cyclopentenone Prostaglandins on Vesicular Stomatitis Virus Replication", Judy Parker et al.*
Journal of Biological Chemistry, 1996, 271(50): 32192–32196; "2–Cyclopenten–1–one, a New Inducer of Heat Shock Protein 70 with Antiviral Activity", Antonio Rossi et al.*
Experientia, 1994, 50(11–12): 1039–1047; "Heat Shock Proteins and Virus Replication: hsp70s as mediators of the Antiviral Effects of Prostaglandins", M. G. Santoro.*
Proc. Nat'l., Acad. Sci. USA, vol. 89, pp. 6227–6231, Jul. 1992 Biochemistry.*
J. Clin. Invest., The American Society for Clinical Investigation, Inc., vol. 93, Mar. 1994, pp. 1087–1094.*
Proc. Nat'l. Acad. Sci. USA, vol. 86, pp. 8407–8471, Nov. 1989, Cell Biology.*
Stress Proteins, Schlesinger, Santoto, Garaci (Eds.) (1990), 3, Induction of HSP70 by Prostaglandins.*
Journal of Virology, Nov. 1994, pp. 6890–6899, 1994, American Society for Microbiology, vol. 68, No. 11.*
Experientia 50, 1994, Birkahuser Verlag, CH–4010 Basel/Switzerland, pp. 1039–1047.*

\* cited by examiner

*Primary Examiner*—Russell Travers
(74) *Attorney, Agent, or Firm*—Hedman, Gibson & Costigan, P.C.

(57) ABSTRACT

The invention relates to 2-cyclopenten-1-one as an inducer of the heat shock protein HSP70 by activating the heat shock transcription factor HSF, and selectively inducing the transcription and translation of HSP70 in human cells. In particular, since a cytoprotective role of HSP70 during viral infection was previously shown, the invention refers to 2-cyclopenten-1-one and its pharmaceutically acceptable derivatives as inducers of HSP70 with antiviral activity. Treatment with 2-cyclopenten-1-one and its pharmaceutically acceptable derivatives causes a dose-dependent reduction of infectious virus yield during infection with vesicular stomatitis virus. The block of virus replication is due to inhibition of viral protein synthesis, associated with HSP70 synthesis.

5 Claims, 2 Drawing Sheets

2-CYCLOPENTEN-1-ONE AS AN INDUCER OF HSP70

The present application is the national stage filing of and claims priority to International Application No. PCT/EP97/03185 filed Jun. 18, 1997 and Italian Application Ser. No. RM96A000430.

FIELD OF THE INVENTION

The present invention relates to 2-cyclopenten-1-one as an inducer of HSP70. In particular the invention relates to 2-cyclopenten-1-one and its pharmaceutically acceptable derivatives as inducers of HSP70 with antiviral activity.

BACKGROUND

As known, prostaglandins (PGs) are a class of naturally occurring cyclic 20-carbon fatty acids that are syntetized by various kinds of eukaryotic cells in response to external stimuli and play an important role in the physiological response to cell proliferation and differentiation. Since their discovery, they were shown to function as microenvironmental hormones and intracellular signal mediators and to control a large number of physiological and pathological processes, including cell proliferation and differentiation, immune response, inflammation, cytoprotection and the febrile response.

In particular, the type A and J PGs, which posses a cyclopentenonic structure, are strong inhibitors of virus replication ("Stress Proteins: Induction and Function" Schlesinger MJ, Garaci E., Santoro M. G. ed.s, Springer-Verlag, Heidelberg-Berlin, 27–44, 1990).

Stress proteins, also called Heat Shock Proteins (HSPs) (Proc. Natl. Acad. Sci. USA 86, 8407–8411, 1989) are a family of polypeptides synthetized by eukaryotic and prokariotyc cells in response to a heat shock or other kinds of environmental stress. The HSPs are encoded by a cellular subgroup of genes, identified as stress genes.

The cytoprotective role of the stress proteins has been described in numerous pathologies, among which ischemia (M.S. Marber et al., J. Clin. Invest. 93, March 1994, 1087–1094).

The authors have shown that some cyclopentenonic prostaglandins (PGA e PGJ) induce the synthesis of heat shock protein HSP70 in human cells through the activation of the heat shock transcription factor HSF (C. Amici et al., Proc. Natl. Sci. USA vol. 89, 6227–6231, 7 1992) It is also known that, in the pathogenesis of the viral infection, the stress proteins HSP interfere at various levels with the virus replication, and in particular a cytoprotective role of the HSP70 protein has been characterized in some experimental models of acute infection (M. G. Santoro, Experientia, Vol. 50, 1039–1047, 1994). The possibility to selectively activate some "heat shock" (hs) genes and to manipulate the cellular stress response to the host advantage is suggested by recent studies which demonstrate that prostaglandins are able to induce HSP70 synthesis in a non-stress situation and to protect the host cell during virus infection (M. G. Santoro, Experientia, Vol. 50, 1039–1047, 1994).

The authors have recently shown that the induction of HSP70 synthesis is one of the molecular mechanisms used by cyclopentenonic prostaglandins to cause a selective and reversible block of the protein synthesis in infection models with single strand negatively polarized RNA viruses (C. Amici et al., J. Virol. 68, 6890–6899, 1994).

In Biol. Pharm. Bull. 18(12)1784–1786 (1995) it is described the cytoprotective activity of the isolated functional groups of several sesquiterpene lactones. Among others 2-cyclopenten-1-one is tested to verify its capability to prevent the formation of gastric lesions induced by various necrotizing agents such as EtOH.

In Antiviral Research 26 (1995) 83–96 it is described the antiviral activity of prostaglandins and a mechanism of action is hypothesized correlating inhibition of VSV RNA polymerase in vitro by prostaglandins with different structures to inhibition of VSV replication in infected cells.

SUMMARY OF THE INVENTION

It has now been found that 2-cyclopenten-1-one, the structure constituting the center nucleus of PGA and PGJ, turns out to have an activity which is analogous to PGA and PGJ, that is, it is able to induce the synthesis of HSP70 protein, even though it does not contain the corresponding acid function and aliphatic lateral chains. Therefore it seems that the lateral chains, which are present in the PGA and PGJ, with their substituents and double bonds, in particular the acid function, which implies the fatty acid nature of prostaglandins, can be eliminated without substantially modifying the herein above described specific activity.

It is therefore an object of the present invention the 2-cyclopenten-1-one as inducer of HSP70.

Another object of the invention is the 2-cyclopenten-1-one as inducer of HSP70 with antiviral activity. Another object of the invention are the 2-cyclopenten-1-one pharmaceutically acceptable derivatives as inducers of HSP70 with antiviral activity.

Further objects of the invention are pharmaceutic compositions comprising 2-cyclopenten-1-one and/or its pharmaceutically acceptable derivatives to make medicaments with antiviral activity. In particular antiviral activity against single strand negatively polarized RNA viruses and DNA viruses. Further objects of the invention will be evident from the following detailed description of the invention.

BRIEF DESCRIPTION OF FIGURES

FIG. 1AII shows the kinetics of HSF (Heat Shock Factor) activation by 2-cyclopenten-1-one. The HSF-HSE complexes were quantitated with a Molecular Dynamics PhosphorImager (MDP).

FIG. 1BII shows the transcription rates, measured by nuclear run-on assay. Following hybridization, the radioactivity was quantitated by MDP analysis.

FIG. 1CII shows the effect of 2-cyclopenten-1-one on protein synthesis. HSP70 synthesis was determined by densitometric analysis of the autoradiograms.

FIG. 2BII shows the effect of 2-cyclopenten-1-one on VSV protein synthesis. VSV infected cells are shown. HSP70 is indicated by the arrow.

DETAILED DESCRIPTION OF THE INVENTION

The 2-cyclopenten-1-one is a known product, which can be synthetized according to the process described in Beilstein (Daene, Eder, A. 539 [1939] 207, 211).

Figure 1:
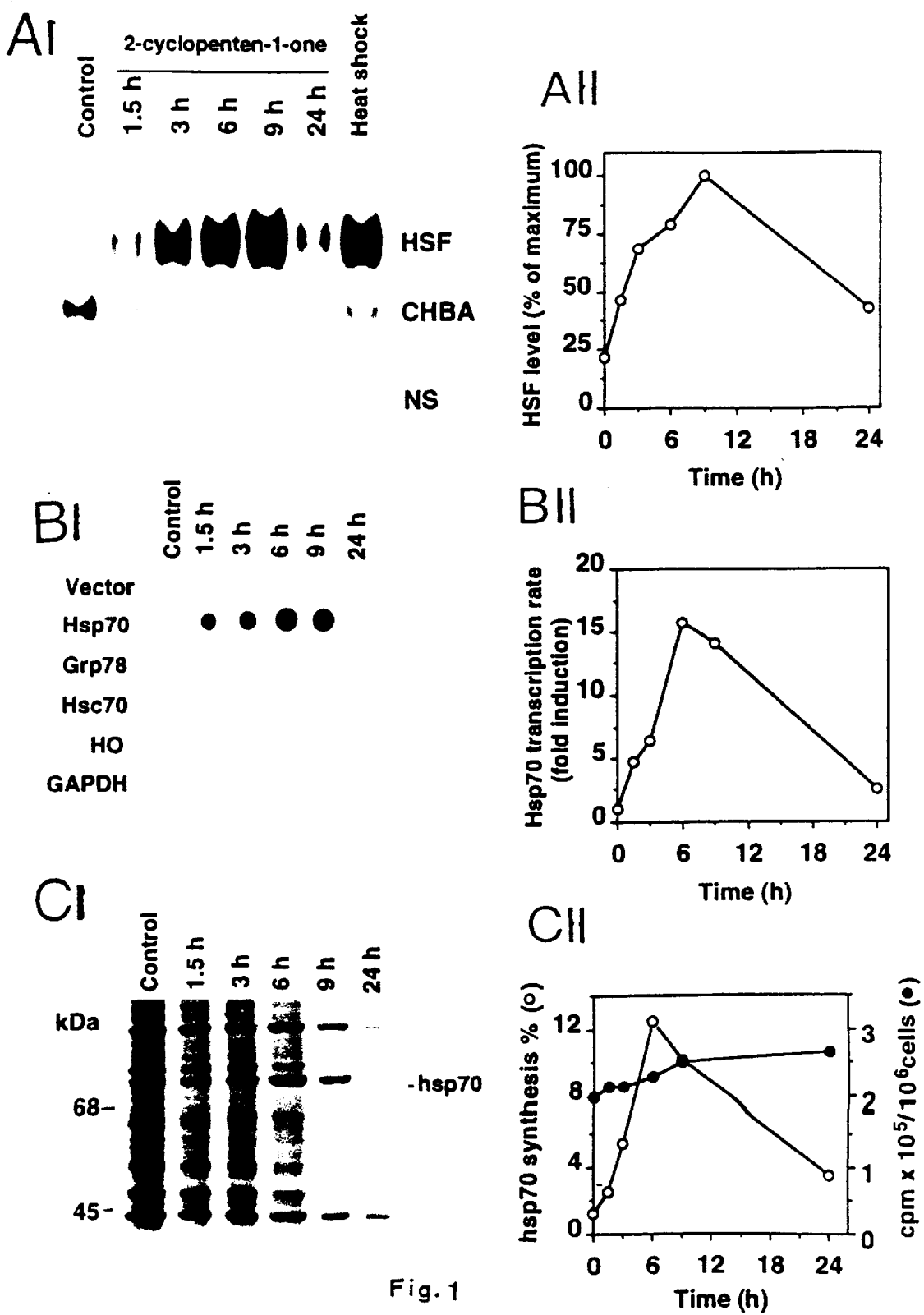
FIG. 1AI shows the kinetics of HSF (Heat Shock Factor) activation by 2-cyclopenten-1-one. Whole cell extracts were subjected to EMSA.
FIG. 1BI shows the transcription rates, measured by nuclear run-on assay. Following hybridization, filters were visualized by autoradiography.
FIG. 1CI shows the effect of 2-cyclopenten-1-one on protein synthesis. Cells were processed for autoradiography.

According to the present invention 2-cyclopente-1-one, preferably in concentration ranging between 100 and 500 µM, can activate the HSF transcription factor and selectively induce the transcription and translation of the HSP70 gene. In particular, induction tests have been performed on human erythroleukemia cells (K562 cells), as shown in FIG. 1.

Figure 2:
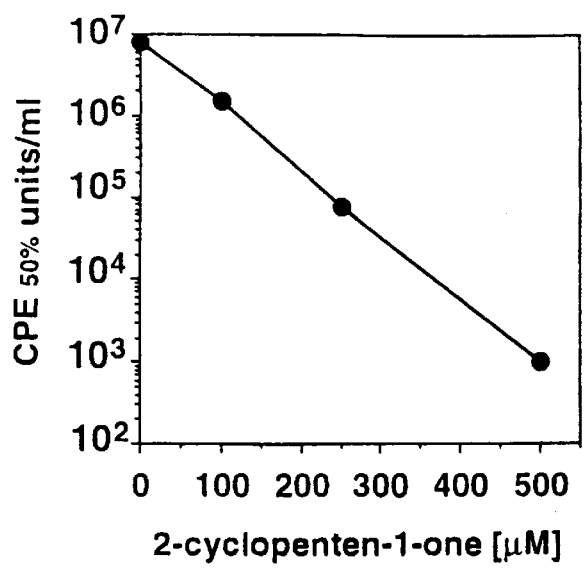
FIG. 2A shows the effect of 2-cyclopenten-1-one on VSV replication. The VSV titers are shown.
FIG. 2BI shows the effect of 2-cyclopenten-1-one on VSV protein synthesis. Uninfected cells are shown.
Figure 2:
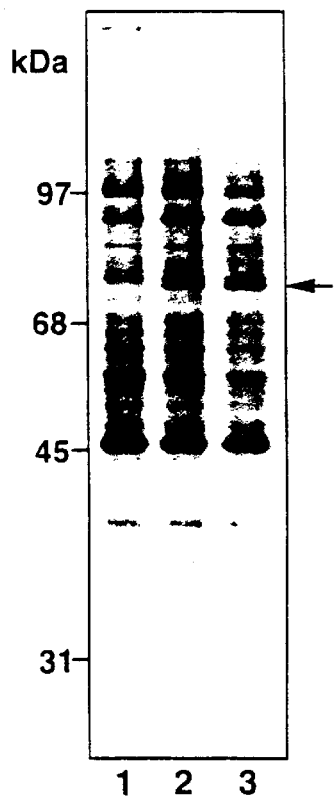
Figure 2:

The HSP70 synthesis was detected also in other types of human cells (HEp-2, HeLa) and in monkey epithelial cells (MA104 cells) (FIG. 2) treated with 2-cyclopenten-1-one. Moreover, the induction of HSP70 synthesis is found to be associated with high antiviral activity. Infact, in MA104 cells infected with the Vesicular Stomatitis Virus (VSV) (1–10P.F.U./cell) the treatment with 2-cyclopenten-1-one, started 1 hour after infection, causes a dose-dependent reduction in the production of infectious viral particles (FIG. 2A). As in the case of other HSP70 inducers, the block in the replication of the virus is caused by the selective inhibition of the synthesis of viral proteins, associated with the synthesis of HSP70 protein (FIG. 2B).

These results confirm the antiviral activity of 2-cyclopenten-1-one as inducer of HSP70 and show the possibility of using 2-cyclopenten-1-one to induce the synthesis of HSP70 and inhibit viral replication. Based on these results it is possible to use 2-cyclopenten-1-one, as well as its pharmaceutically acceptable derivatives, as active substances to produce medicaments, in particular medicaments having antiviral activity against negative strand RNA viruses and DNA viruses, sensitive to the antiviral activity of cyclopentenonic prostaglandins.

It is an advantage of the invention to have a product with antiviral action at low costs for its synthesis and a novel mechanism of antiviral action, different from antiviral drugs in use. The following examples are reported to illustrate the invention. They should be considered in any case non limiting the scope of the invention itself.

The reagents used in the examples, including 2-cyclopenten-1-one, were products of Sigma Aldrich. $^{32}P$ e $^{35}S$ were produced by AMERSHAM. Fetal calf serum and cellular culture media were produced by GIBCO.

EXAMPLE I

The effect of the treatment with 2-cyclopenten-1-one on the HSF activation, on the heat shock gene transcription and on the synthesis of the proteins have been evaluated in K562 cells with the methods described hereinbelow and shown in FIG. 1.
KINETICS OF ACTIVATION The cells were prepared according to the method described in C. Amici et al. Cancer Research 55, 4452–4457, 1995.

Whole-cell extracts, prepared at different times after treatment with 500 µM of 2-cyclopenten-1-one in ethanol or after 3 hours of heat shock (45° C. for 20 min) were subjected to EMSA (Electrophoretic Mobility Shift Assay) (FIG. 1AI), as described in C. Amici et al. Cancer Research 55, 4452–4457, 1995. The positions of HSF, CHBA (HFS-DNA constitutive activity) and NS (proteins-DNA non-specific interaction) are indicated. The levels of HSF DNA-binding activity in cells treated with 2-cyclopente-1-one were quantitated with a Molecular Dynamics PhosphorImager (MDP) (FIG. 1AII). The HSF values were normalized to the level of HSF DNA-binding activity at 9 h after treatment, which was given a value of 100%.

As evident, 2-cyclopenten-1-one is able to activate HSF. The activation is prolonged for the following 24 hours, with a maximum at 9 hours from the beginning of the treatment.

TRANSCRIPTION RATE OF HSP70 GENE.

The transcription rates were measured by Nuclear Run-On assay (C. Amici et al., Cancer Research 55, 4452–4457, 1995). The $^{32}P$-labelled RNA was hybridized to nitrocellulose filters containing plasmids for the following human genes: hsp70 (pH,2,3; B. Wu et al., Mol. Cell. Biol. 5, 330 (1985)); grp78/BiP (glucose-regulated 78 protein) (pHG 23,1; C. Amici et al., Proc. Natl. Acad. Sci. USA 89, 6227, 1992); hsc70 (heat shock cognate 70) (pHA 7,6; C. Amici et al., Proc. Natl. Acad. Sci. USA 89, 6227, 1992); HO (heme oxygenase) (HO clone 2/10; A. Rossi e M. G. Santoro, Biochem. J., 308, 455, 1995); GAPDH (rat glyceraldehyde phosphate dehydrogenase) (GAPDH, 1400 bp, PstI; A. Rossi e M. G. Santoro, Biochem. J., 308, 455, 1995). The vector plasmid (Bluescript) was used as a non-specific hybridization control. Following hybridization, the filters were visualized by autoradiography (FIG. 1BI) and the radioactivity was quantitated by MDP analysis (FIG. 1BII). The values are expressed as arbitrary units obtained by comparing transcription rates to control levels. As evident, 2-cyclopenten-1-one is able to selectively activate the hsp70 gene transcription. The transcription is prolonged at high levels for at least 9 hours from the beginning of the treatment.

EFFECT OF 2-CYCLOPENTEN-1-ONE ON HSP70 PROTEIN SYNTHESIS Equal amounts of protein from K562 cells labeled with [$^{35}S$]-methionine (10 µCi/10$^6$ cells, 1 h pulse) at different times after treatment with 500 µM 2cyclopenten-1-one were analyzed on 10% SDS/PAGE gels and processed for autoradiography (FIG. 1CI) Hsp70 synthesis (?) was determined by densitometric analysis of the autoradiograms (FIG. 1CII). Total protein synthesis (?) was determined as [$^{35}S$]-methionine incorporation into TCA-insoluble material (C. Amici et al., Exp. Cell. Res. 207, 230–234, 1993).

As evident, 2-cyclopenten-1-one is able to selectively stimulate HSP70 protein synthesis at concentrations that do not inhibit the cellular protein synthesis.

EXAMPLE II

The effect of 2-cyclopente-1-one on the replication of Vesicular Stomatitis Virus (VSV) and on the HSP70 protein synthesis was evaluated as described in the following and illustrated in FIG. 2. Confluent nonolayers of monkey kidney MA104 cells, grown in RPMI-1640 medium supplemented with 5% FCS (fetal calf serum) and antibiotics, were infected with VSV (Indiana serotype, Orsay; 1 P.F.U./cell). After 1 h at 37° C., the viral inoculum was removed and cells were kept at 37° C. in RPMI-1640 medium containing 2% FCS and different concentrations of 2-cyclopenten-1-one in ethanol or control diluent. VSV titers were determined 24 h post infection (p.i.) by cytopathic effect 50% (CPE 50%) assay, as described in F. Pica et al., Antiviral Res., vol. 20, 193, 1993 and illustrated in FIG. 2A.

Uninfected (U) or VSV-infected (VSV) MA104 cells were treated with 250 µM (lanes 2 and 5) and 500 µM (lanes 3 and 6) 2-cyclopenten-1-one, or with control diluent (lanes 1 and 4), soon after VSV infection and labeled with [$^{35}S$]-methionine (8 µCi/2×10$^5$ cells, 1 h pulse starting 5 h p.i.). Equal amounts of protein were analyzed on 10% SDS/PAGE gel and processed for autoradiography. The position of hsp70, identified by western blot analysis using anti-human hsp70 antibodies, is indicated by the arrow. VSV proteis L, G, N, NS and M are indicated. 2-cyclopenten-1-one, at concentrations ranging between 100 and 500 µM, inhibits the production of VSV infectious virions from 10 to more than 1000 times with respect to the control, under the indicated conditions. The inhibition is mediated by a selective block of the viral protein synthesis, combined with the induction of HSP70.

What is claimed is:

1. A method for the treatment of a viral infection comprising the administration of a pharmaceutically effective amount of 2-cyclopenten-1-one or its pharmaceutically acceptable derivatives to a host having a viral infection in a amount which is effective to induce the production of Heat Shock Protein HSP70.

2. The method according to claim 1 wherein the 2-cyclopenten-1-one is administered to provide a concentration ranging between 100 and 500 $\mu$M.

3. The method as defined in claim 1 which is based on the administration of pharmaceutically effective doses of 2-cyclopenten-1-one to a host with a viral infection to induce the the production of Heat Shock Protein HSP70.

4. The method as defined in claim 1 which is based on the administration of 2-cyclopenten-1-one and its pharmaceutically acceptable derivatives to induce the production of Heat Shock Protein HSP70 against single strand negatively polarized RNA viruses and DNA viruses.

5. A method for the treatment of a viral infection comprising contacting a cell which is infected with a virus with an amount of 2-cyclopenten-1-one or its pharmaceutically acceptable derivatives which is effective to provide a concentration of from 100 to 500 $\mu$M in said cells to induce the production of Heat Shock Protein HSP70.

* * * * *